(12) United States Patent
Corcoran et al.

(10) Patent No.: US 11,284,871 B2
(45) Date of Patent: Mar. 29, 2022

(54) UNCOUPLED LAA DEVICE

(71) Applicant: Cardia, Inc., Eagan, MN (US)

(72) Inventors: Michael Patrick Corcoran, Woodbury, MN (US); Joseph A. Marino, Apple Valley, MN (US); Englong Tan, Maplewood, MN (US)

(73) Assignee: Cardia, Inc., Eagan, MN (US)

( * ) Notice: Subject to any disclaimer, the term of this patent is extended or adjusted under 35 U.S.C. 154(b) by 374 days.

(21) Appl. No.: 16/599,442

(22) Filed: Oct. 11, 2019

(65) Prior Publication Data
US 2020/0038004 A1 Feb. 6, 2020

Related U.S. Application Data

(63) Continuation of application No. 15/625,375, filed on Jun. 16, 2017, now Pat. No. 10,441,258.

(51) Int. Cl.
*A61B 17/00* (2006.01)
*A61M 29/00* (2006.01)
*A61B 17/12* (2006.01)

(52) U.S. Cl.
CPC .... *A61B 17/0057* (2013.01); *A61B 17/12031* (2013.01); *A61B 17/12122* (2013.01);
(Continued)

(58) Field of Classification Search
CPC .......... A61B 17/0057; A61B 17/12031; A61B 17/12172; A61B 17/12122;
(Continued)

(56) References Cited

U.S. PATENT DOCUMENTS 3,874,388 A 4/1975 King
4,007,743 A 2/1977 Blake
(Continued)

FOREIGN PATENT DOCUMENTS

EP 0362113 A1 4/1990
EP 0541063 B1 8/1998
GB 2269321 A 2/1994

OTHER PUBLICATIONS

Apr. 23, 2013 PCT Search Report (Serial No. PCT/US13/027061)—Our Matter 4972.
(Continued)

*Primary Examiner* — Phong Son H Dang
(74) *Attorney, Agent, or Firm* — Forsgren Fisher; James M. Urzedowski; Daniel A. Tysver (57) ABSTRACT

A medical device for treating an LAA is presented. The device includes a cap, a bulb and a joint assembly therebetween. The cap is a three layer mesh structure with a retaining hub securing the layers together. A plurality of proximal wire loops extend from the base layer to a proximal post of the joint assembly. The bulb has a plurality of distal wire loops that extend between a terminal post and a distal post of the joint assembly. The joint assembly comprises a first ball joint, a second ball joint and a housing. Each ball joint is retained in the housing independent ball and socket relationships. Each ball joint and post defines a longitudinal axis. The housing defines a housing longitudinal axis. By way of the ball and socket relationship each ball joint longitudinal axis may form an angle of between about 0 to about 35 degrees with the housing longitudinal axis in any direction.

10 Claims, 13 Drawing Sheets

(52) U.S. Cl.
CPC ....... *A61B 17/12172* (2013.01); *A61M 29/00* (2013.01); *A61B 2017/00579* (2013.01); *A61B 2017/00592* (2013.01); *A61B 2017/00597* (2013.01); *A61B 2017/00632* (2013.01)

(58) Field of Classification Search
CPC ........... A61B 2017/00632; A61B 2017/00597; A61B 2017/00579; A61B 2017/00592; A61M 29/00
See application file for complete search history.

(56) References Cited

U.S. PATENT DOCUMENTS

| | | |
|---|---|---|
| 4,284,166 A | 8/1981 | Gale |
| 4,917,089 A | 4/1990 | Sideris |
| 5,092,424 A | 3/1992 | Schreiber |
| 5,108,420 A | 4/1992 | Marks |
| 5,171,259 A | 12/1992 | Inoue |
| 5,284,488 A | 2/1994 | Sideris |
| 5,334,137 A | 8/1994 | Freeman |
| 5,334,217 A | 8/1994 | Das |
| 5,382,260 A | 1/1995 | Dormandy, Jr. |
| 5,397,331 A | 3/1995 | Himpens |
| 5,425,744 A | 6/1995 | Fagan |
| 5,433,727 A | 7/1995 | Sideris |
| 5,451,235 A | 9/1995 | Lock |
| 5,634,936 A | 6/1997 | Linden |
| 5,649,950 A | 7/1997 | Bourne |
| 5,702,421 A | 12/1997 | Schneidt |
| 5,709,707 A | 1/1998 | Lock |
| 5,725,552 A | 3/1998 | Kotula |
| 5,741,297 A | 4/1998 | Simon |
| 5,904,703 A | 5/1999 | Gilson |
| 6,024,756 A | 2/2000 | Huebsch |
| 6,171,329 B1 | 1/2001 | Shaw |
| 6,174,322 B1 | 1/2001 | Schneidt |
| 6,206,907 B1 | 3/2001 | Marino |
| 6,355,052 B1 | 3/2002 | Neuss |
| 6,379,368 B1 | 4/2002 | Corcoran |
| 6,389,146 B1 | 5/2002 | Croft, III |
| 6,511,496 B1 | 1/2003 | Huter |
| 6,551,344 B2 | 4/2003 | Thill |
| 6,634,455 B1 | 10/2003 | Yang |
| 6,689,150 B1 | 2/2004 | Vantassel |
| 6,712,836 B1 | 3/2004 | Berg |
| 7,044,134 B2 | 5/2006 | Khairkhahan |
| 7,097,653 B2 | 8/2006 | Freudenthal |
| 7,582,104 B2 | 9/2009 | Corcoran |
| 7,735,493 B2 | 6/2010 | Van Der Burg |
| 7,905,901 B2 | 3/2011 | Corcoran |
| 7,938,826 B2 | 5/2011 | Davis |
| 8,257,389 B2 | 9/2012 | Chanduszko |
| 8,480,706 B2 | 7/2013 | Chanduszko |
| 8,480,709 B2 | 7/2013 | Chanduszko |
| 8,764,848 B2 | 7/2014 | Callaghan |
| 9,554,804 B2 | 1/2017 | Erzberger |
| 9,861,346 B2 | 1/2018 | Callaghan |
| 2003/0195555 A1 | 10/2003 | Khairkhahan |
| 2004/0093022 A9 | 5/2004 | Kurz |
| 2005/0038470 A1 | 2/2005 | Van Der Burg et al. |
| 2005/0043759 A1 | 2/2005 | Chanduszko |
| 2005/0065547 A1 | 3/2005 | Marino |
| 2005/0273135 A1 | 12/2005 | Chanduszko |
| 2005/0277982 A1 | 12/2005 | Marino |
| 2006/0241687 A1 | 10/2006 | Glaser |
| 2007/0010851 A1 | 1/2007 | Chanduszko |
| 2007/0244518 A1 | 10/2007 | Callaghan |
| 2008/0039929 A1 | 2/2008 | Davis |
| 2008/0086168 A1 | 4/2008 | Cahill |
| 2009/0076541 A1 | 3/2009 | Chin |
| 2009/0099647 A1 | 4/2009 | Glimsdale |
| 2009/0171386 A1 | 7/2009 | Amplatz |
| 2009/0292310 A1 | 11/2009 | Chin |
| 2011/0082495 A1 | 4/2011 | Ruiz |
| 2012/0065667 A1 | 3/2012 | Javois |
| 2012/0172927 A1 | 7/2012 | Campbell |
| 2012/0316602 A1 | 12/2012 | Chanduszko |
| 2013/0218192 A1 | 8/2013 | Erzberger |
| 2013/0218193 A1 | 8/2013 | Erzberger |
| 2013/0289618 A1 | 10/2013 | Chanduszko |
| 2014/0142610 A1 | 5/2014 | Larsen |
| 2015/0005810 A1 | 1/2015 | Center |
| 2017/0258475 A1 | 9/2017 | Mellmann |

OTHER PUBLICATIONS

Apr. 29, 2013 PCT Search Report (Serial No. PCT/US13/027065)—Our Matter 4973.
Dec. 31, 2013 USPTO Office Action (U.S. Appl. No. 13/763,929)—Our Matter 4930.
Apr. 1, 2014 PCT Preliminary Examination Report (Serial No. PCT/US13/027065)—Our Matter 4973.
Jul. 2, 2014 USPTO Office Action (U.S. Appl. No. 13/400,968)—Our Matter 4794.
Aug. 12, 2014 USPTO Office Action (U.S. Appl. No. 13/763,929)—Our Matter 4930.
Jun. 16, 2015 USPTO Office Action (U.S. Appl. No. 13/400,968)—Our Matter 4794.
Jun. 18, 2015 USPTO Office Action (U.S. Appl. No. 13/763,929)—Our Matter 4930.
Feb. 24, 2016 USPTO Office Action (U.S. Appl. No. 13/763,929)—Our Matter 4930.
Sep. 12, 2016 USPTO Office Action (U.S. Appl. No. 13/400,968)—Our Matter 4794.
May 30, 2019 USPTO Office Action (U.S. Appl. No. 15/625,375)—Our Matter 5494.
Mar. 22, 2013 USPTO Office Action (U.S. Appl. No. 13/400,968)—Our Matter 4794.
Nov. 22, 2013 USPTO Office Action (U.S. Appl. No. 13/400,968)—Our Matter 4794.
Feb. 6, 2014 PCT Preliminary Examination Report (Serial No. PCT/US13/027061)—Our Matter 4972.
Nov. 2, 2015 USPTO Office Action (U.S. Appl. No. 13/400,968)—Our Matter 4794.

UNCOUPLED LAA DEVICE

CROSS-REFERENCE TO RELATED APPLICATIONS

The present application is a continuation application of U.S. application Ser. No. 15/625,375, entitled: Uncoupled LAA Device, filed on Jun. 16, 2017 and issued as U.S. Pat. No. 10,441,258 on Oct. 15, 2019; the entire contents of which are incorporated herein by reference.

FIELD OF THE INVENTION

The present invention relates to implanted devices for use in occluding the left atrial appendage (LAA) of patients. The device includes structures that permit the device to be easily retrieved and redeployed, as well as structures that provide improved articulation and flexibility to allow the device to be deployed in the LAA regardless of size, shape or angle of insertion presented by a patient's anatomy.

BACKGROUND OF THE INVENTION

The heart is generally comprised of four chambers: the left and right atrium, and the left and right ventricle. Additionally, a small cavity called the left atrial appendage (LAA) is located off the left atrium between the mitral valve and the left pulmonary vein. Thus, the LAA opens into the left atrium of the heart. The LAA is shaped like a small thumb which terminates as it tapers away from the opening. The opening itself is referred to as the LAA ostium.

In a healthy heart, the LAA contracts as the heart contracts. In individuals diagnosed with atrial fibrillation (AF), however, the LAA may not contract with enough force to expel all of the blood from the LAA. In individuals diagnosed with AF, the electrical activity of the atrium becomes very rapid and disorganized. Thus, the heart beats quickly and may not get enough time in between beats to fill up with blood. As a result, only a small amount of blood is pumped out of the heart with each beat, and the cardiac output drops significantly. Therefore, stagnant blood may easily remain in the LAA. Because clotting occurs when blood is stagnant, clots or thrombi may form in the LAA. If a blood clot leaves the LAA and becomes lodged in an artery in the brain, a stroke results.

The LAA may be sealed off during open heart surgery, which is a risky, painful, and expensive procedure. Surgery for closure of the LAA is major heart surgery, which requires the patient to undergo general anesthesia and opening of the chest cavity. The patient must spend several days in the hospital and thereafter may take several weeks to be able to return to normal levels of activity.

To avoid the risks and discomfort associated with open heart surgery, modem occlusion devices have been developed that are small, implantable devices capable of being delivered to the heart through a catheter. Rather than surgery, a catheter inserted into a major blood vessel allows an occlusion device to be deployed at the defect once the device has been moved through the catheter to the treatment site. This procedure is performed in a cardiac cathlab and avoids the risks and pain associated with open heart surgery. These devices have proven effective at sealing defects in the heart and could likewise be used to occlude the LAA without requiring open heart surgery.

Devices that have received significant clinical study include the "Plaato" device described in U.S. Pat. No. 6,152,144 among others, and the "Watchman" device described in U.S. Pat. No. 6,689,150 among others. Each of these clinically tested devices lies wholly within the LAA and includes a membrane that spans the opening or ostium of the LAA. The Watchman device is typically porous and in the Plaato device the membrane is impervious to the passage of blood. Additionally, the Watchman device uses a series of barbs or prongs which enter the tissue surrounding the ostium of the left atrial appendage to help secure the device during the acute phase of implant.

While devices such as these have been shown to be effective for occluding the LAA, they nevertheless have drawbacks. For example, such devices are often incapable of being readily deployed in anatomies having irregularities such as an oddly shaped LAA or that extends at sharp angles from the atrial wall. Similarly, such devices employ occluding baskets or cages of wire mesh that though flexible, may impose their shape on the LAA causing the LAA to be distended or irritated leading to potential post implantation complications. The ability to retrieve and redeploy the devices which may be necessary to achieve proper placement is also problematic with these existing devices. In most instances a retrieved device may not be reused and must be replaced, driving the cost of the therapy up.

Thus, there is a need in the art for an LAA occlusion device which can be implanted at a wide variety of approach angles and that may be implanted into the LAA without distorting the shape of the LAA or causing undue irritation thereto; and which is redeployable to facilitate reliable implantation.

SUMMARY

The devices and their methods of use described herein differ from prior LAA devices and techniques by providing a device that includes a cage or bulb for deployment within the LAA space that while still supportive of the LAA is more flexible than previous devices. In addition, the device includes an articulated joint between the bulb and ostial cap which allows the relative position between the cap and bulb to be angled or skewed to a greater degree than known LAA occlusion devices. Devices of the present disclosure may also include a unique three-layer cap structure which while pliant and conformable to the shape of the ostium of the LAA, also provides a seal that prevents the passage of clots therethrough with superior performance over known cap structures.

These and other unique features provide for embodiments of the disclosure that provide LAA devices, which are highly adaptable for use in any anatomy, and which provide superior LAA occlusion characteristics.

DETAILED DESCRIPTION

Figure 1:
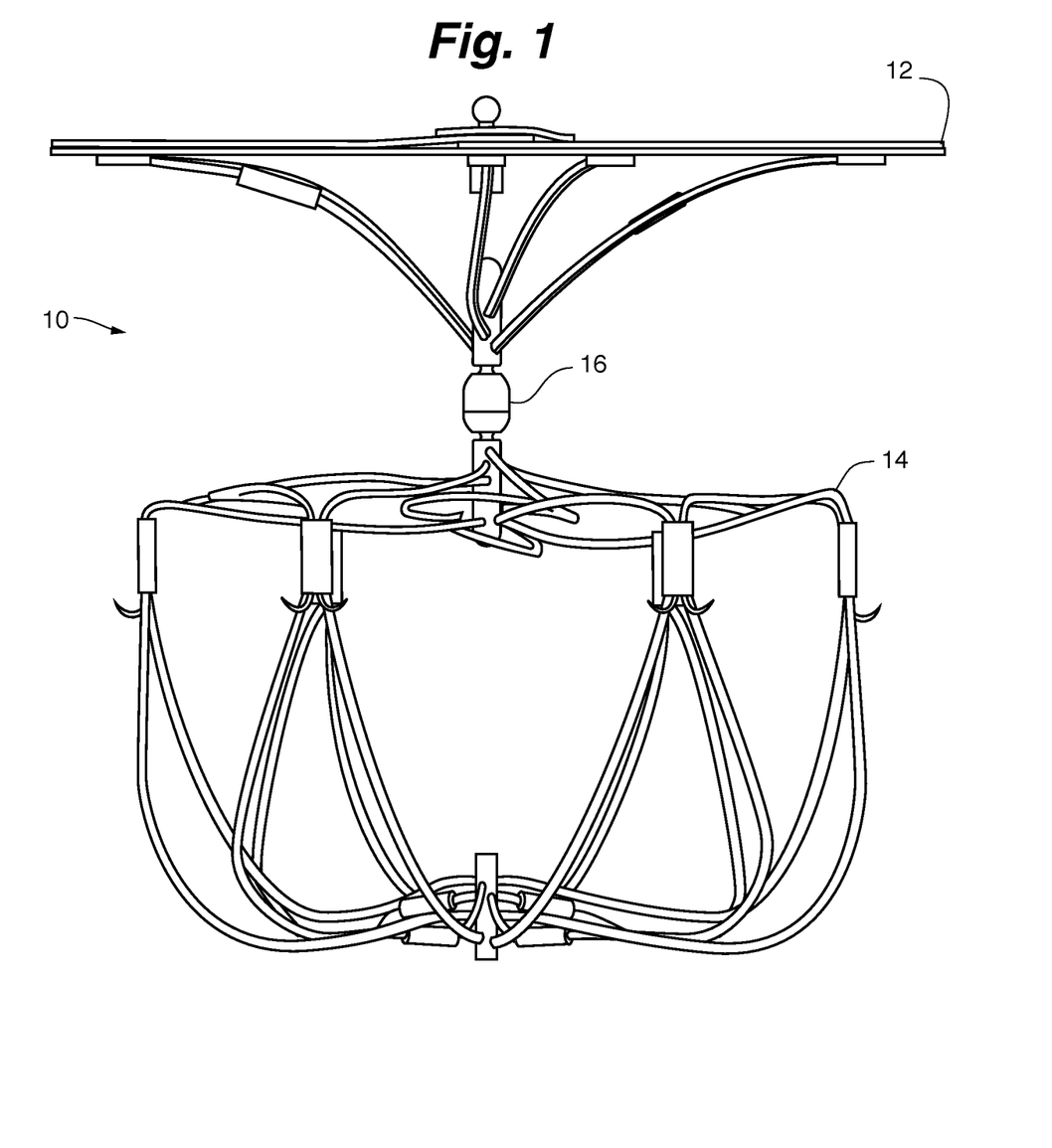
FIG. 1 is a side view of an embodiment of an LAA occlusion device shown in the deployed or fully expanded state.

FIG. 1 shows the LAA device 10 shown in its fully expanded configuration. The device includes a cap structure 12 and a cage or bulb structure 14. A connection joint assembly 16 provides a pivoting and rotatable joint between the cap 12 and bulb 14.

Figure 2:
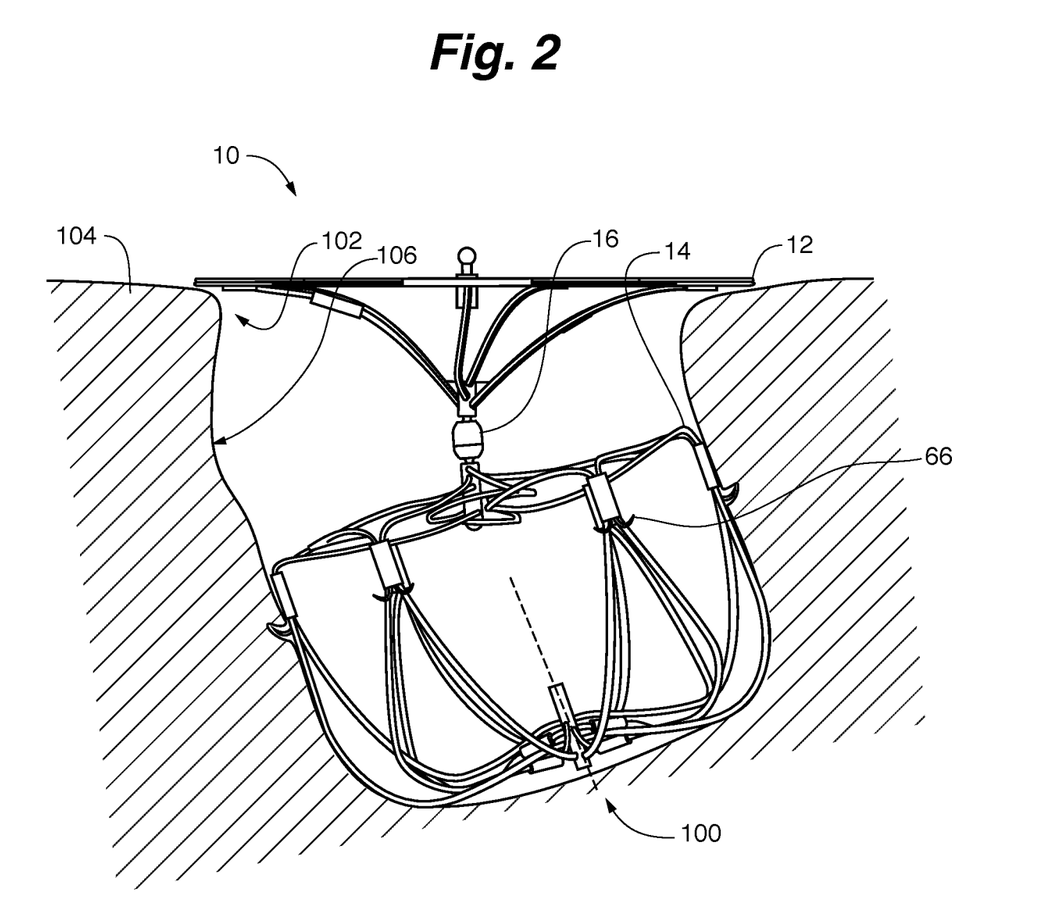
FIG. 2 is a side view of the embodiment shown in FIG. 1 wherein the device is shown deployed in its environment of use.

FIG. 2 shows the device 10 deployed within its intended environment of use within the left atrial appendage (LAA) 100. When properly deployed the cap structure 12 over-lies the annular ostium 102 of the LAA 100 with the larger perimeter of the cap engaging or being positioned immediately adjacent to the surrounding atrial tissue 104. The bulb structure 14, when properly deployed, engages the walls 106 of the LAA without distortion or application of force sufficient to distend or alter the shape of the LAA. The connection joint assembly 16 allow the cap 12 and bulb 14 to be moved and deployed effectively independent of one another, thus allowing the cap 12 to have a secure engagement across the ostium 102 and the bulb 14 to be firmly positioned within the LAA 100 regardless of the shape, or tortuosity of the anatomy.

Figure 3:
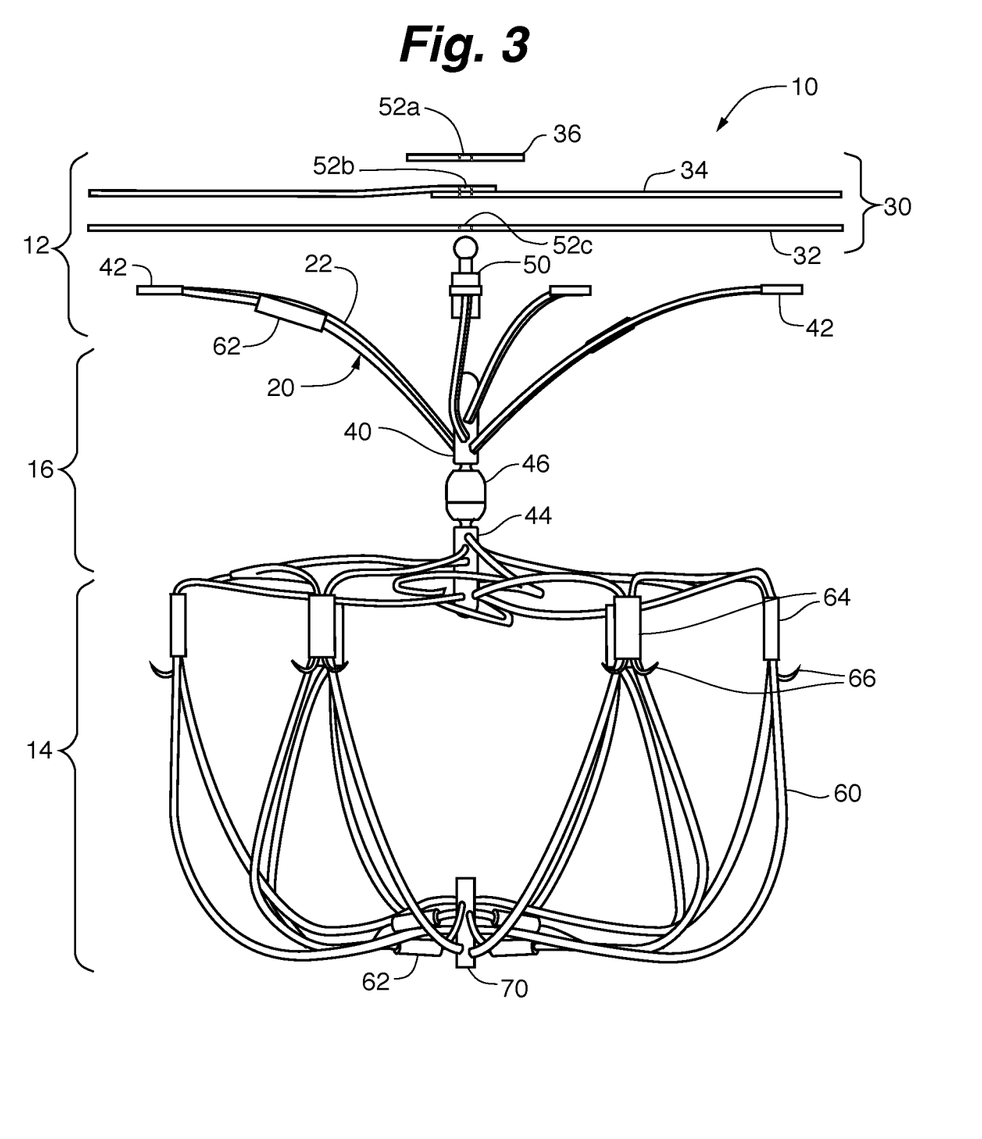
FIG. 3 is an exploded side view of the embodiment shown in FIG. 1
Figure 4:
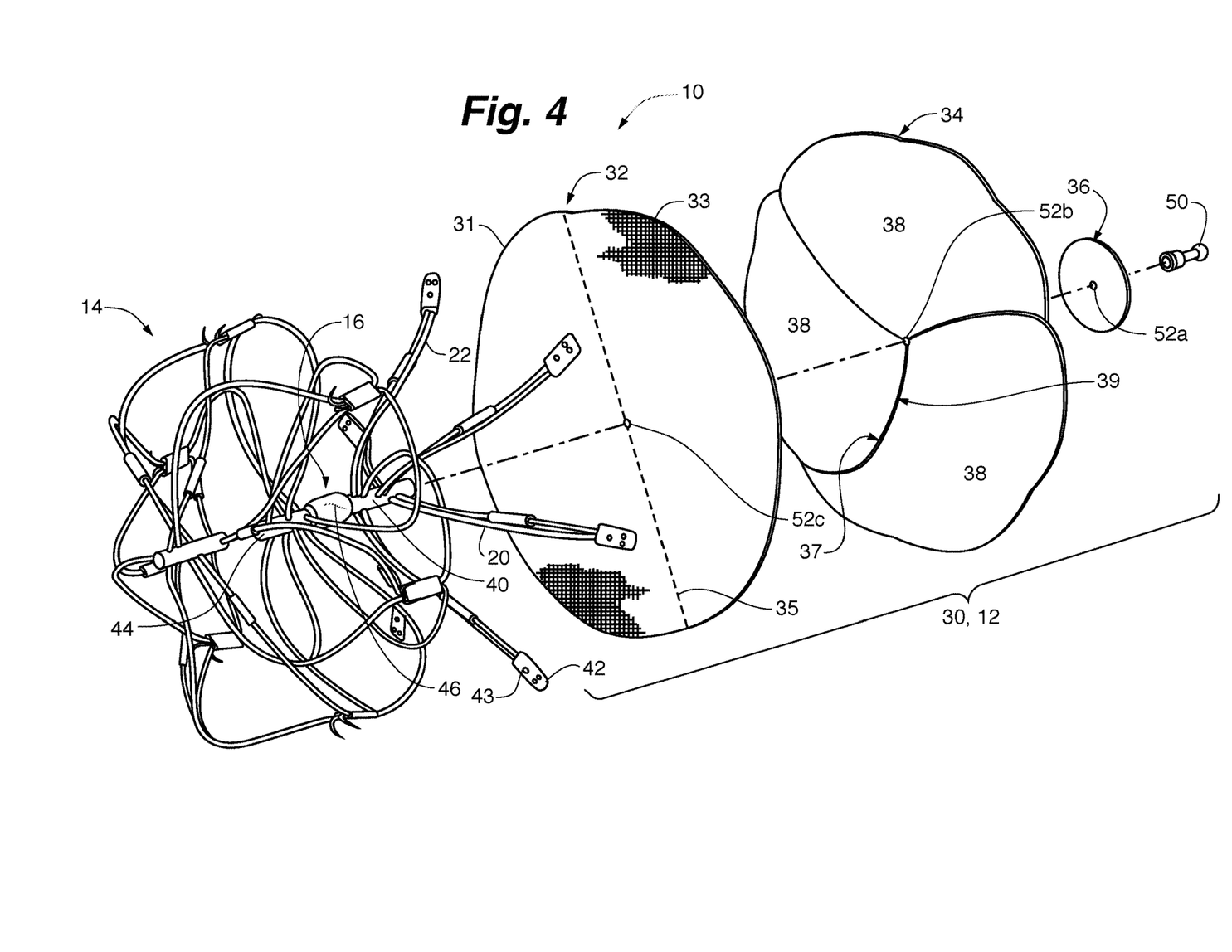
FIG. 4 is an exploded perspective view of the embodiment shown in FIGS. 1-3.

Turning to the exploded view depictions of the device 10 show in FIGS. 3 and 4, here the components of the cap structure 12 and their unique construction are more clearly shown. The cap 12 is comprised of a plurality of proximal wire supports or loops 20 that extend from the base layer 32 of the sail or ostial cover 30. Each proximal wire loop 20 may be comprised of a single wire 22 (which may be a stranded wire of multiple wire filaments with a larger core filament surrounded by up to 12 smaller diameter filaments) of a shape memory material such as Nitinol. The wire 22 extends from the proximal post 40 of the joint assembly 16 (discussed in greater detail below) to a connection member 42, whereupon the wire 22 loops back to the post 40 to complete the structure of the wire loop 20. Each connection member 42 includes a plurality of through holes 43 (best seen in FIG. 4) through with a bio-compatible filament or braid (not shown) may be threaded to secure the cover 30 to each wire loop 22.

In the embodiment shown in FIG. 3-4, the cover 30 is a representative multilayer structure having a base layer 32 and secondary or "petal" layer 34 and a top layer 36. Base layer 32 and petal layer 34 are comprised of mesh of any of a variety of bio-compatible materials such as: polyethylene terephthalate, polyester (DACRON™), Polyvinyl Alcohol (PVA), polyurethane, etc. Layers 32 and 34 may have same of different porosity and may be woven or manufactured with different thicknesses or other characteristics.

The base layer 32 may be a single unitary piece of mesh material, or as in the embodiment shown in FIG. 4, comprised of two hemi-spheres 31 and 33 of material joined together along a common border 35 by sutures or other retaining mechanism. In some embodiments, the base layer is comprised of multiple joined sections of material of any number desired. The junction of the sections 31 and 33 of the base layer may be achieved by suturing or other engagement mechanism, or by simply allowing the portions to abut or overlap one another at or along the border 35. By providing a base layer 32 of multiple sections, tissue in growth is promoted along the border 35 of the sections 31 and 33 even if the porosity of the mesh prevents or limits such growth.

Turning now to the secondary layer 34, here multiple sections or petals 38 of ovoid or elliptical shaped material are arranged in a continuous and overlapping manner with a front edge 37 of a given petal 38 positioned either under or over the back edge 39 of the immediately adjacent petal 38. As with the border(s) 35 of the base layer 32, the overlapping arrangement of petals 38.

Finally, the top or securement layer 36 of material is a layer of substantially solid or tightly woven or extruded mesh material having greater strength than the under lying layers 32 and 34. The securement layer's primary function is to act as a buffer and securement surface for securing the cover 30, as a whole, to an engagement hub 50. Each layer 32, 34 add 36 defines a central opening or hole 52a, 52, b and 52c (respectively). Through which a portion (or shaft) of the engagement hub 50 passes so as to cinch the layers of the cover 30 together and hold them in place adjacent one another; while simultaneously ensuring that the cover 30 has sufficient strength to resist tearing or disruption during the crimping and/or delivery process discussed in greater detail below.

Turning now to the bulb or cage structure 14, as shown in FIGS. 1-4 and best seen in FIG. 3, the bulb structure 14 is made up of a collection of distal wire loops 60. The distal wire loops 60 comprise a single wire or wire braid 22 that passes through the distal post 44 of the joint assembly 16 and extend to the terminal post 70; with the ends of the wire 22 of each distal loop 60 collected in a crimp coupler 62. A companion collar 64 connects the wire 22 of adjacent distal wire loops 60, to provide structural stability and support to the bulb structure 14. The collars 64 connect immediately adjacent wire loops and permit forces to be shared by the two loops while not influencing other wire loops of the bulb structure 14.

The collars 64 also include barbs 66, which extend distally from each coupler 64. The barbs 66 are sized and arranged such that when the bulb 14 is deployed into the LAA 100, such in the manner shown in FIG. 2, the barbs 66 engage the walls 106 of the LAA, thereby ensuring that the bulb 14 maintains its secure position within the LAA space indefinitely once fully deployed therein.

Though the collars 64 provide the bulb structure 14 with support and structural stability, it must be noted that the arrangement of wire loops 60 is such that when the bulb 14 is fully deployed within the space of the LAA 100, the bulb will minimally (if at all) distort, distend or otherwise affect the size or shape of the LAA.

Figure 6:
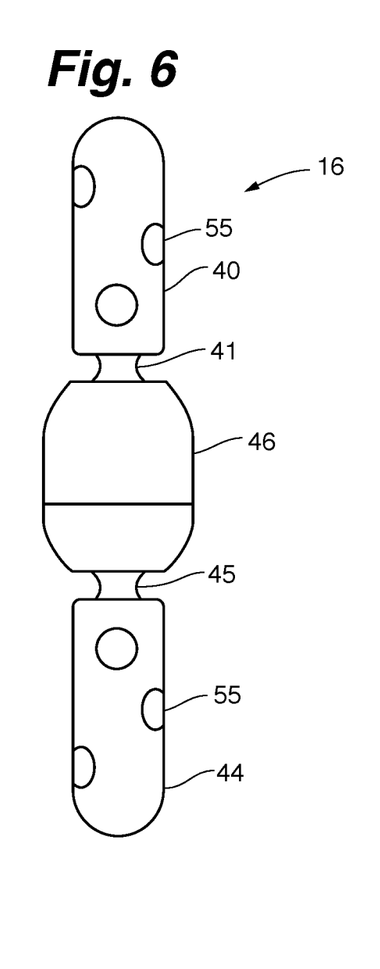
FIG. 6 is a close-up side view of the connection joint shown in FIG. 5.
Figure 7:
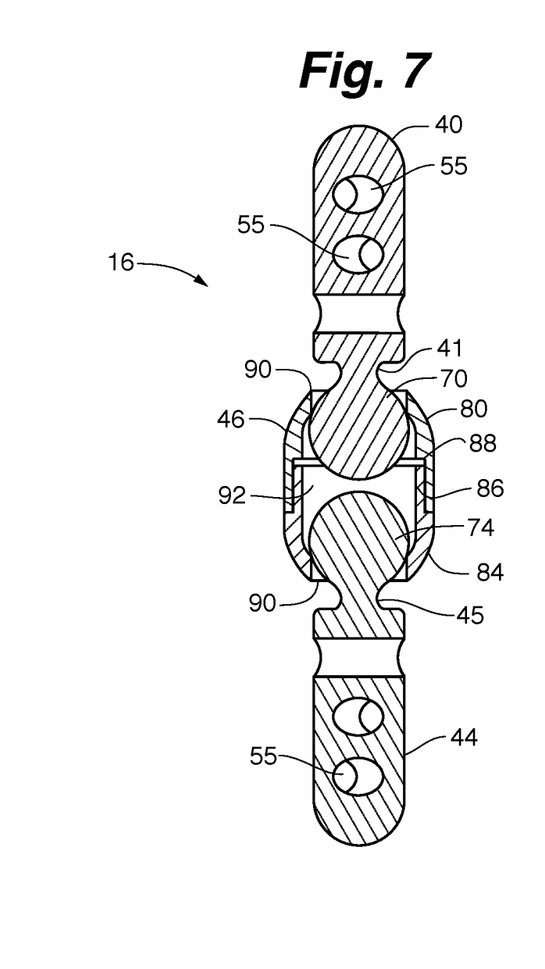
FIG. 7 is a sectional view of the connection joint shown in FIG. 6.
Figure 8:
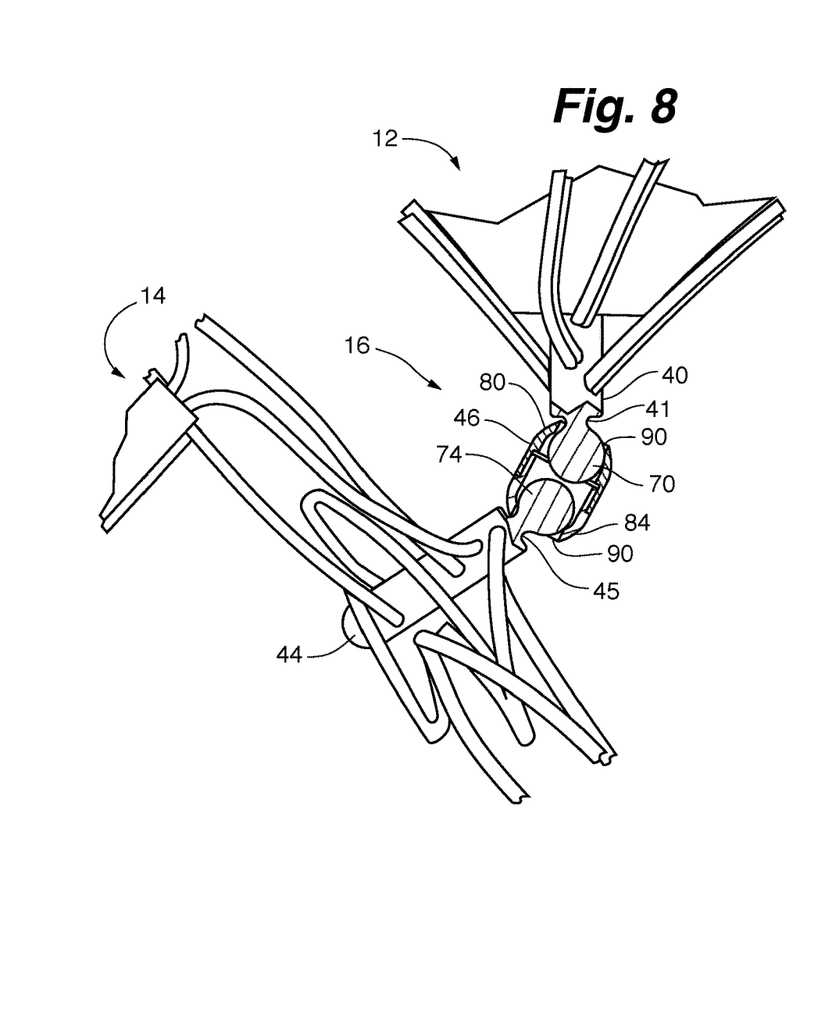
FIG. 8 is a close-up view of the embodiment shown in FIG. 5 with the connection joint shown in section to illustrate its ability to provide and limit articulation between the cap and bulb.
Figure 9:
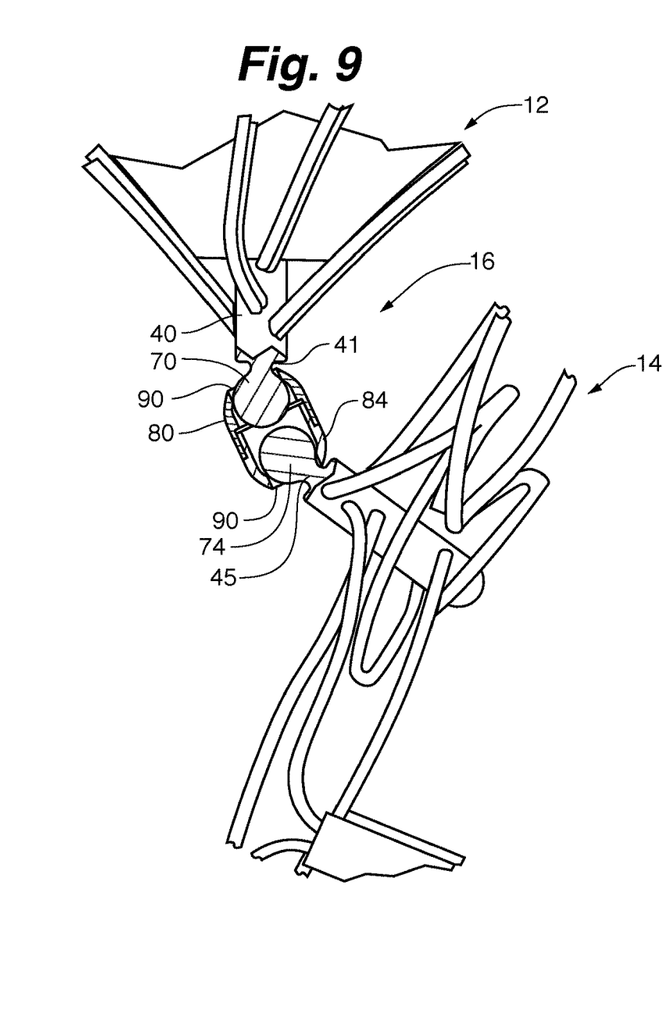
FIG. 9 is an alternative close-up view of the embodiment shown in FIG. 5 with the connection joint shown in section to illustrate its ability to provide and limit articulation between the cap and bulb.
Figure 10:
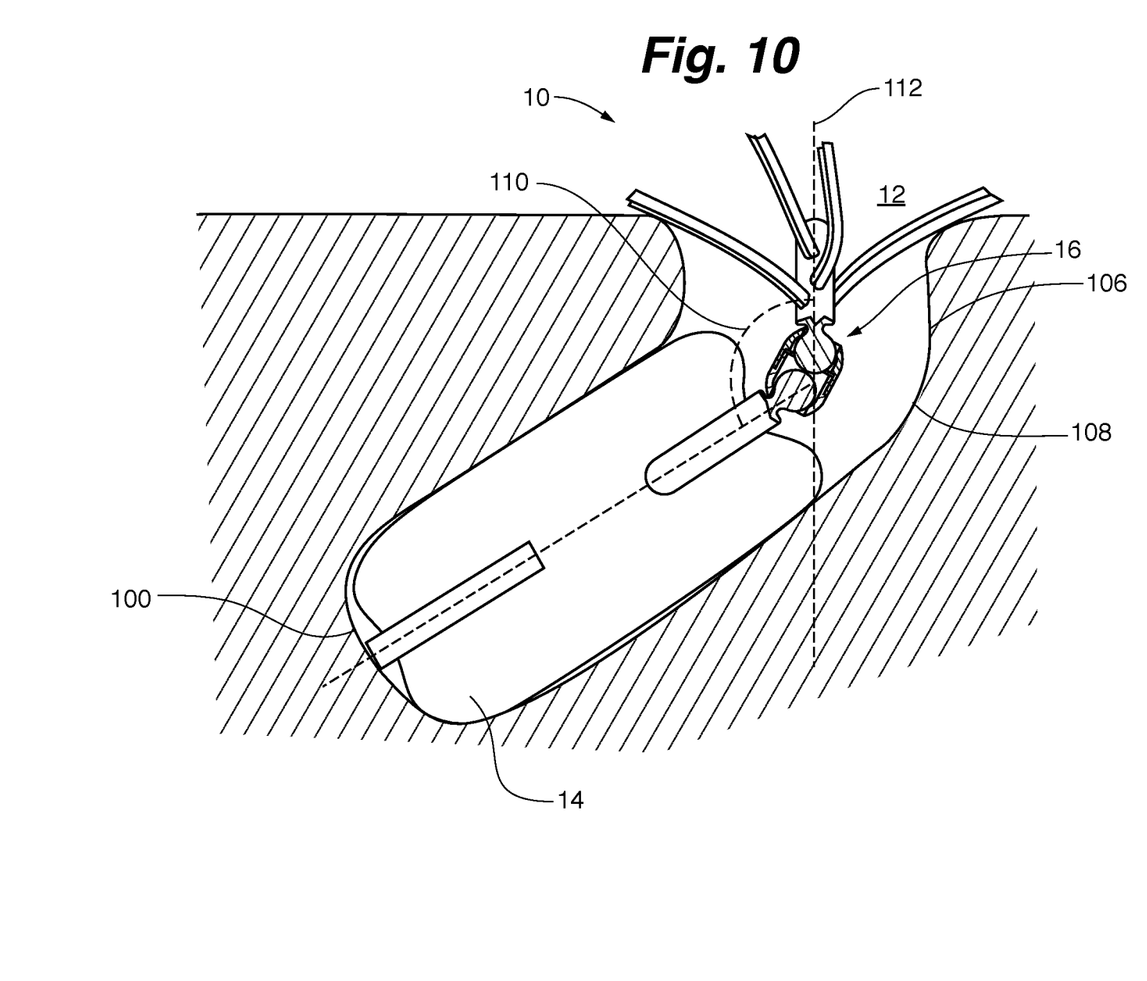
FIG. 10 is a side view of the device shown in FIG. 5 deployed within a left atrial appendage having a curved shape.

As mentioned above, positioned between cap structure 12 and bulb structure 14 is a joint assembly 16, such as is shown in FIG. 1-4. Externally, the joint assembly 16 comprises the aforementioned proximal post 40 to which the wire loops 20 of the cap structure 12 are threaded and engaged; a distal post 44 to which the wires 22 of wire loops 60 of the bulb structure 14 are threaded and engaged. An end of each post 40 and 44 are held movable adjacent one another within a joint housing 46. Openings 55 of the posts 40 and 44, through which the wires 22 of the respective structures 12 and 14 are engaged are depicted in FIGS. 6-7.

Figure 5:
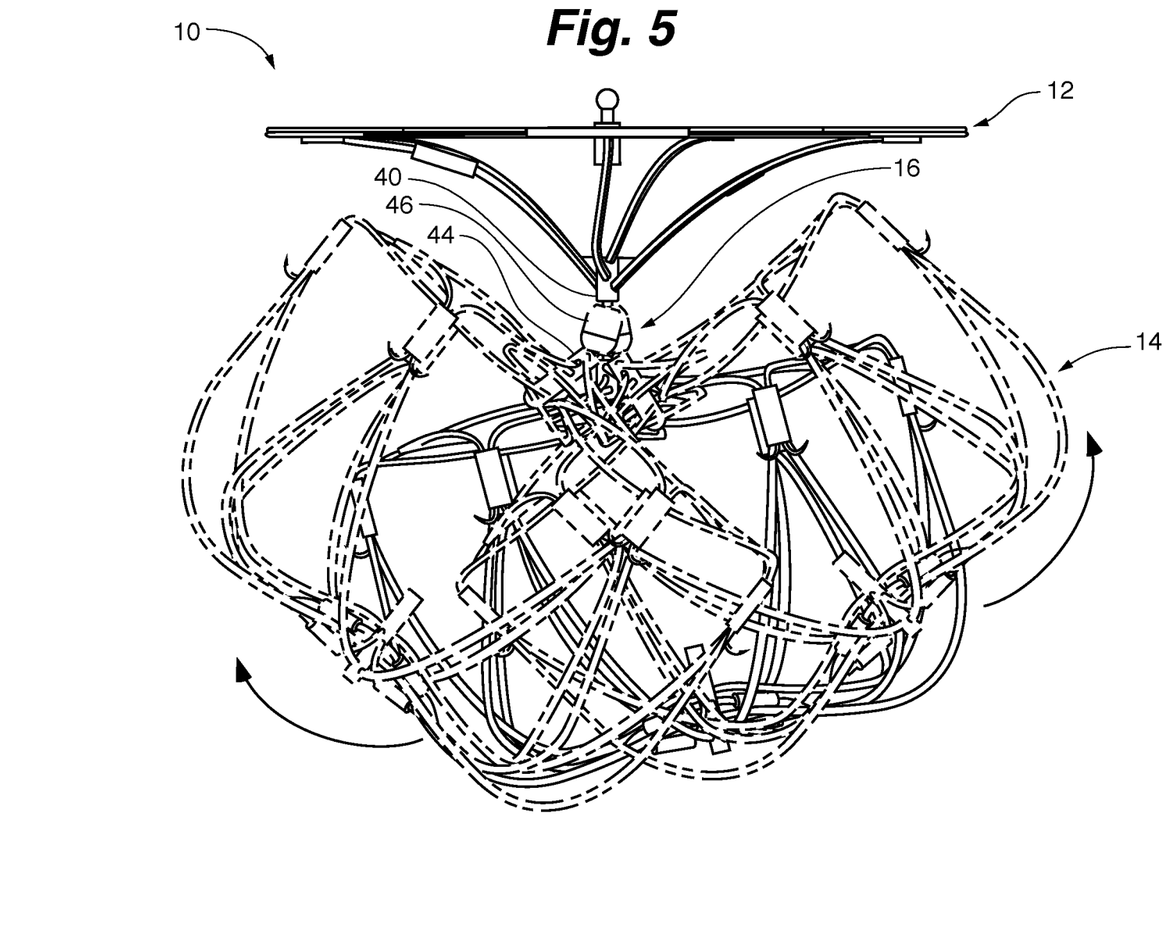
FIG. 5 is a side view of an embodiment of the LAA occlusion device shown in FIG. 1 depicting the degree of potential articulation between the cap and the bulb via the connection joint.

In one embodiment, shown in FIG. 5 the particular arrangement of the post 40 and 44 ends within the joint housing 46 and the unique structure of the housing 46 provides the device 10 with a fluid connection between the cap structure 12 and bulb structure 14, allowing the bulb structure 14 to be rotationally and pivotally articulated relative to the cap structure 12 to a degree limited only by the interference presented by the aforementioned structures themselves, or by the limitations provided by the joint assembly 16, such as in the manner described below.

The particular manner in which the cap 12 and bulb 14 are articulable relative to one another, via the joint assembly 16, is shown in FIGS. 6-10. Looking to FIG. 7, the internal configuration of the joint assembly 16 is shown. As can be seen, proximal post 40 includes a proximal neck 41 that terminates at a first or Wdrasler@comcast.netfirst ball joint 70 and distal post 44 includes a distal neck 45 that terminates at a second or second ball joint 74. As shown, the ball joints are not complete "balls" but merely the rounded aspect of the joint assembly. Their specific shape and dimensions may vary and the particular manner in which they engage with or extend from their respective necks (41/45) may likewise be varied. In some embodiments, the ball joints are ellipsoid or oval in shape. In at least one embodiment they are substantially spherical in shape above the interface with the neck. In at least one embodiment the ball joints have a flattened or "bone shaped" end.

Preferably, a hard metal, such as titanium or other similar material suitable for use in medical implantation, is used to construct the parts of the joint assembly 16 including the housing 46, shafts 40 and 44, etc. The first ball joint 70 is contained within a first sleeve 80 of the joint housing 46 and the second ball joint 74 is contained within a second sleeve 84 of the joint housing 46, such that each sleeve 80/84 of the housing 46 forms the "socket" for moveably retaining the "ball" of the respective ball joint 70/74 in proximal and distal "ball and socket" type connections.

Second sleeve 84 includes a cuff or collar 86 which supports a washer 88 and biases the washer 88 between the first sleeve 80 and second sleeve 84. Each sleeve has a sleeve opening 90. The sleeve openings 90 if larger in diameter than the diameter of the proximal neck 41 or distal neck 45 which passes through a respective opening 90, but narrower in diameter than the diameter of the first ball joint 70 or second ball joint 74 thereby retaining the ball joints 70 and 74 within the interior 92 of the joint housing 46.

The sleeves 80 and 84 which comprise the joint housing 46 are mechanically secured to one another, or may be chemically or heat welded or together.

When arranged in the manner shown in FIGS. 6 and 7, the aforementioned components result in a joint assembly 16 wherein two ball joints 70 and 74 are able to rotate and pivot independently of each other relative to the housing 46. The ball joints 70 and 74 are separated by the washer 88 so that they do not come in contact with each other and restrict each other's movement. The washer 150 also prevents the ball joints 70 and 74 from moving too far into the center of the sleeves 80 and 84.

The diameter of the openings 90 relative to the diameter of the necks 41 and 45 likewise acts as a limit on the degree of motion that the shafts 40 and 44 are able to demonstrate relative to the housing 46. This is perhaps best shown in FIGS. 8-9 wherein the extreme limits of the pivotal movement of shafts 40 and 44 are illustrated by the interaction of the opening 90 with the necks 41 and 45. By providing fairly generous opening diameter relative to that of the necks 41 and 45 the shafts 40 and 44 may be provided with an extreme amount of motion, thereby allowing the cap 12 and bulb 14 a corresponding amount of articulation relative to the joint assembly 16 and to one another as illustrated in FIG. 5.

In use, this high degree of articulation allows the device 10 to be successfully deployed into left atrial appendages having even the most tortuous of shapes. For example, in the embodiment shown in FIG. 10, the device 10 is deployed within an LAA 100 whose walls 106 define a sock-like shape having a substantially angled curve or bend 108. The bend 108 may define an angle 110 of up to about 70 degrees relative to the longitudinal axis 112, as defined by the walls 106, which define the initial LAA opening (ostium 102). Because of the high degree of articulation provided by the joint assembly 16, the present device may be deployed in even the most curvaceous of left atrial appendages without undue strain on the surrounding anatomy.

Figure 11:
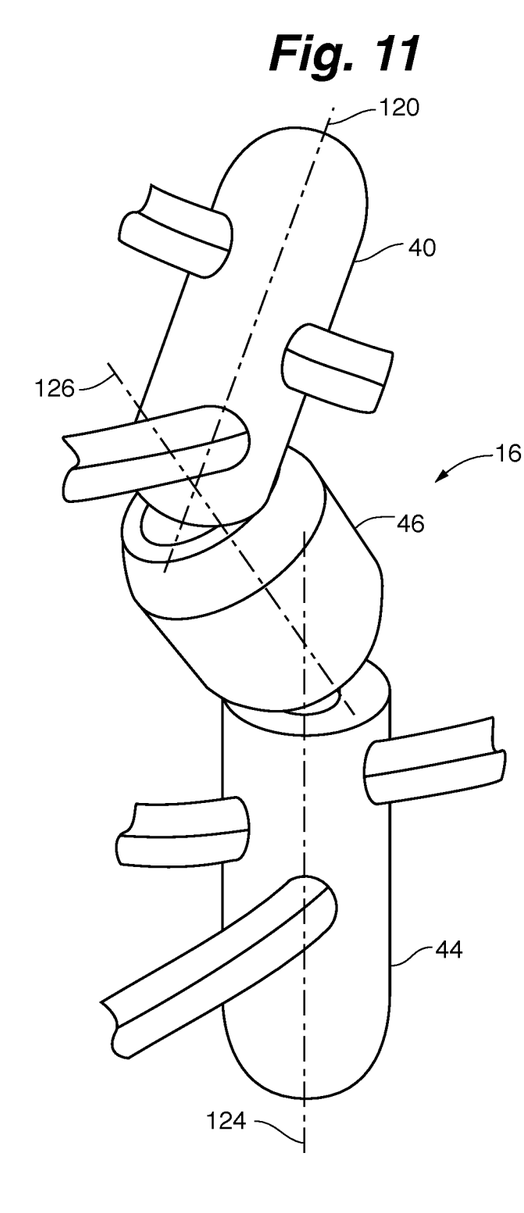
FIG. 11 is a detailed perspective view of the joint assembly illustrating its three potential axes of rotation and articulation.
Figure 12:
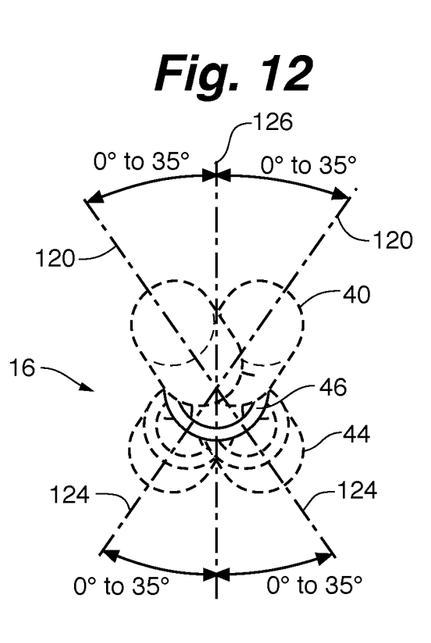
FIG. 12 is a top down perspective view of the joint assembly shown in FIG. 11 depicting the potential full range of motion of the joint assembly components.

The high degree of flexibility that the joint assembly 16 exhibits, provides the device 10 not only with the ability to be deployed around a bend but to deploy around a bend in three dimensions such as in the manner illustrated in FIGS. 11-12. Here the joint assembly 16 is shown relative to three axes of articulation and rotation 120, 124 and 126. Proximal post 40 extends along the proximal axis of rotation 120; distal post 44 extend along the distal axis of rotation 124. Each post 40 and 44 (by way of the first ball joint 70 and the second ball joint 74 as previously discussed) are separately articulable in any direction relative to the housing axis of rotation 126 which corresponds to and extends along the length of the joint assembly housing 46. By this assembly and arrangement, each post 40 and 44—and by extension the cap 12 and bulb 14 respectively engaged thereto (not shown, see FIG. 10)—may be positioned and form an angle with the housing 46 that is different from one another and in any direction. In other words: the cap 12 and bulb 14 components may each be positioned in such a manner as to form angles along their respective axis of rotation, in any direction, relative to the housing 46 of the joint assembly 16 of between 0 to approximately 35 degrees respectively.

Figure 13:
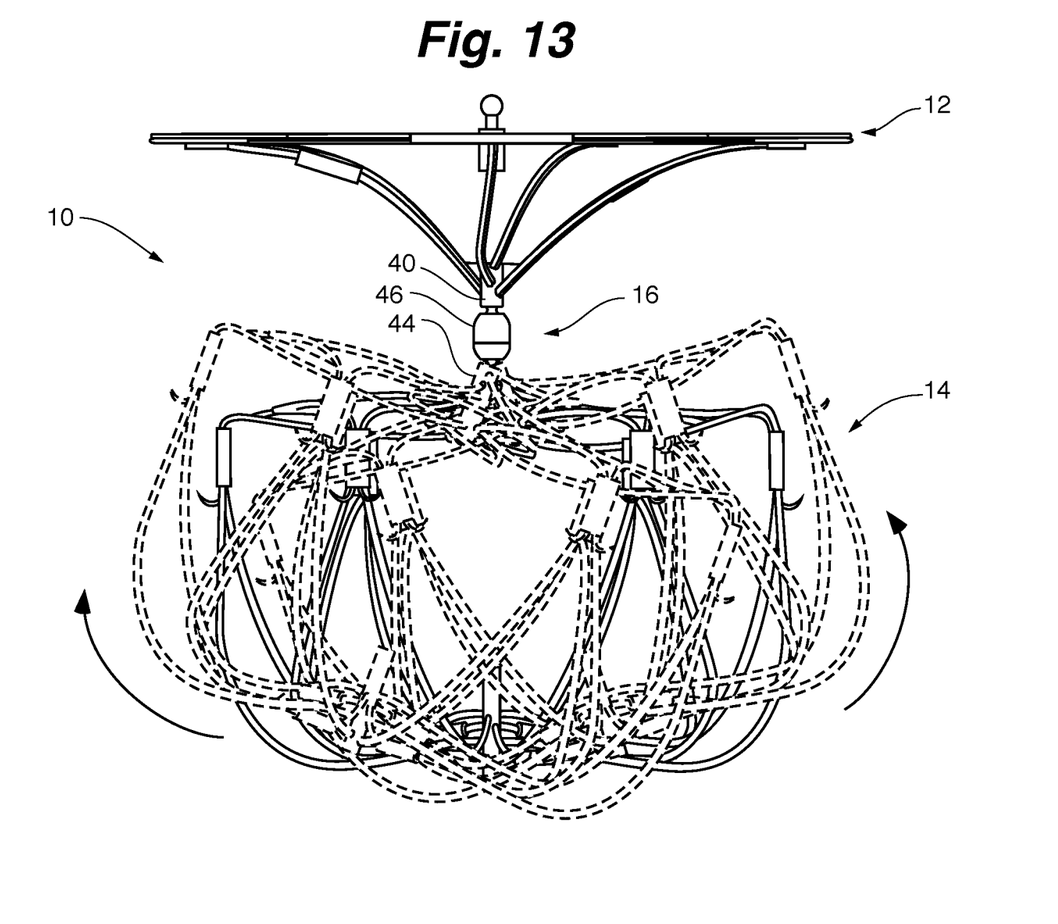
FIG. 13 is a side view of an alternative embodiment of the LAA occlusion device shown in FIG. 5.
Figure 14:
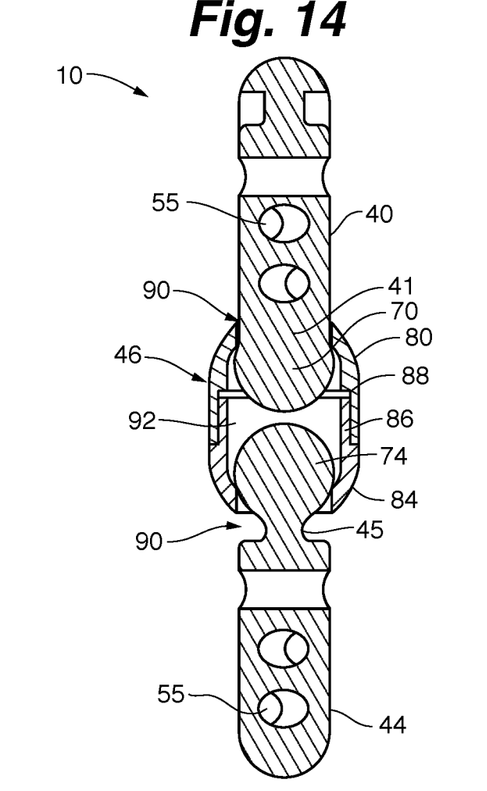
FIG. 14 is a close-up side view of the connection joint assembly shown in FIG. 10.
Figure 15:
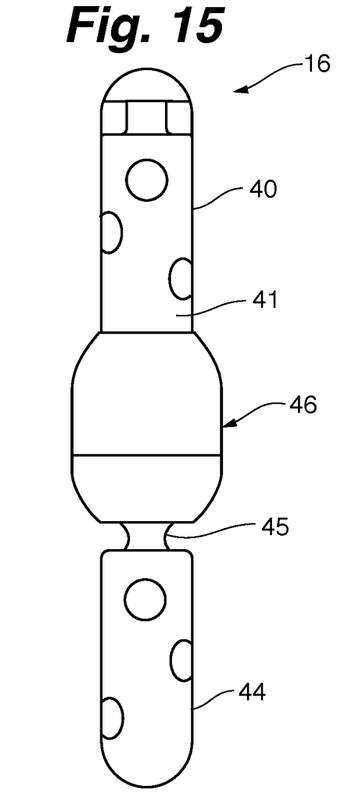
FIG. 15 is a sectional view of the connection joint assembly shown in FIG. 11.

A device 10 having such extreme flexibility is not ideal however in all cases. In fact, an unrestricted degree of rotational and pivotal movement may in some cases make the implantation of the device 10 into an LAA more difficult. It has been found through laboratory experimentation that too much articulation on the bulb side (distal) of the joint assembly 16 may in some cases cause complications in properly delivering the device. Thus, in at least some embodiments, an example of which is shown in FIG. 13-15 potential articulation of the shafts 40 and 44 relative to the housing 46 have been limited by modifying the diameter of the opening 90 of sleeve 80 and/or by making the neck 41 of post 40 larger relative to the opening 90 of the sleeve 80 so as to limit the potential motion between the post 40 and housing 46.

If desired, such modification of opening and neck diameters may be provided instead, or in addition to, that described above to the distal neck 45 and sleeve 84, so as to limit the motion between the housing 46 and distal post 44. Any of a variety of relative diameters between the necks 41 and 45 versus the openings 90 may be provided to the device 10 as may be desired.

With the above description, the unique features of the device 10 are made clear. Some of these features include providing a highly variable articulable joint assembly that allows for a wide degree of freedom of movement between the ostial cap and the bulb structure of the device. This allows the device to be oriented in any manner desired and to be adaptable to any LAA location or configuration. In addition, the bulb structure is configured such that when fully deployed within the LAA the bulb does not impact the shape of the LAA space.

Figure 16:
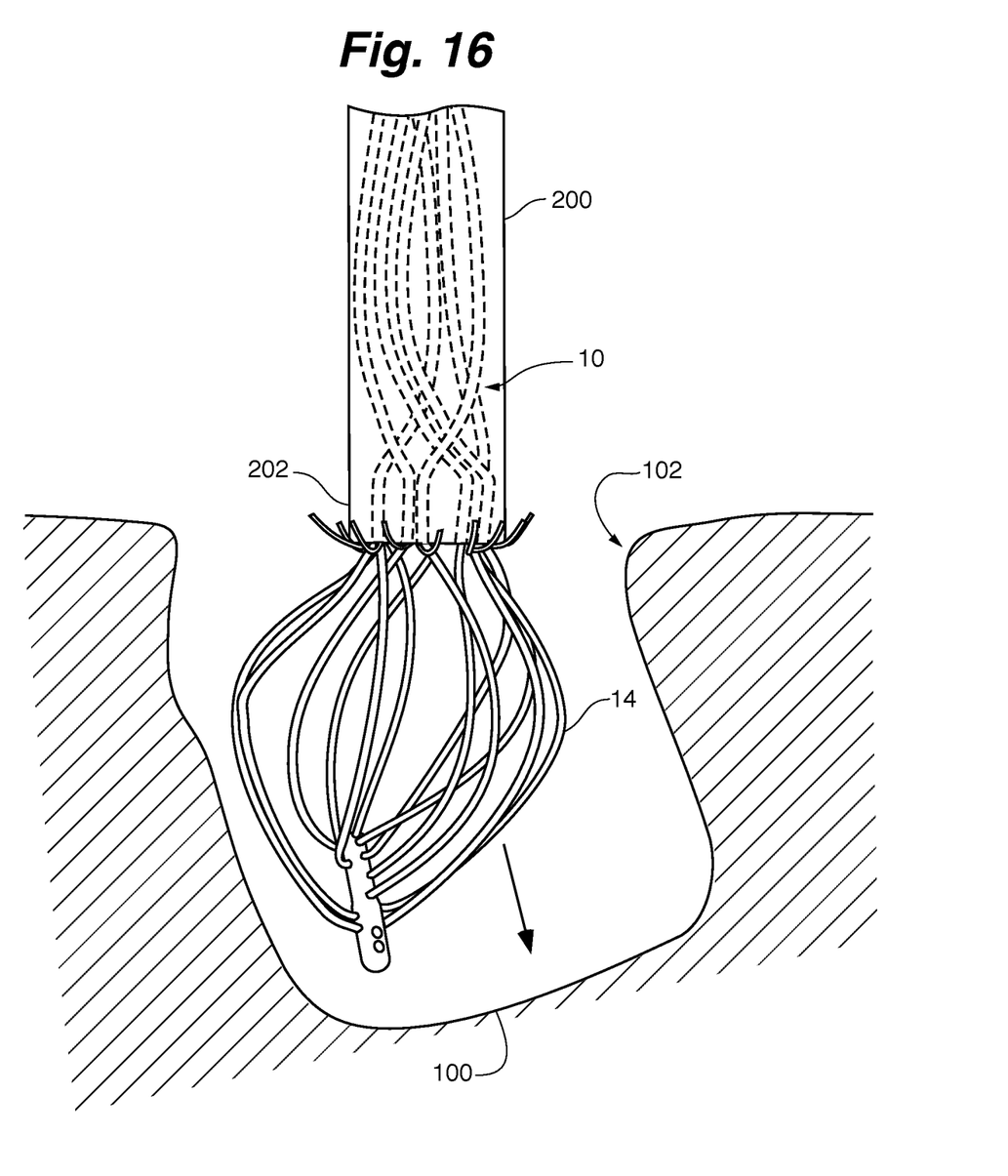
FIG. 16 is a side view of an embodiment of the LAA device being deployed from a catheter and into the LAA.

When delivering the device 10 to the LAA 100 of a patient via catheter 200 such as in the manner shown in FIG. 16, the device 10 is folded or collapsed into a confined state such that the diameter of the device 10 is sufficient to allow the device to be loaded into the interior of a delivery catheter 200. The delivery catheter 200 is advanced in to the left atrium and the delivery tip 202 of the catheter is inserted about 10 mm-20 mm past the ostium 102 of the LAA 100. The device 10 is then advanced out of the catheter (or a delivery sheath his pulled back from the device, etc.) and the bulb structure 14 is advanced into the LAA space where the distal wire loops 60 self-expand to the deployed diameter. The deployed diameter being greater than the confined diameter.

Figure 17:
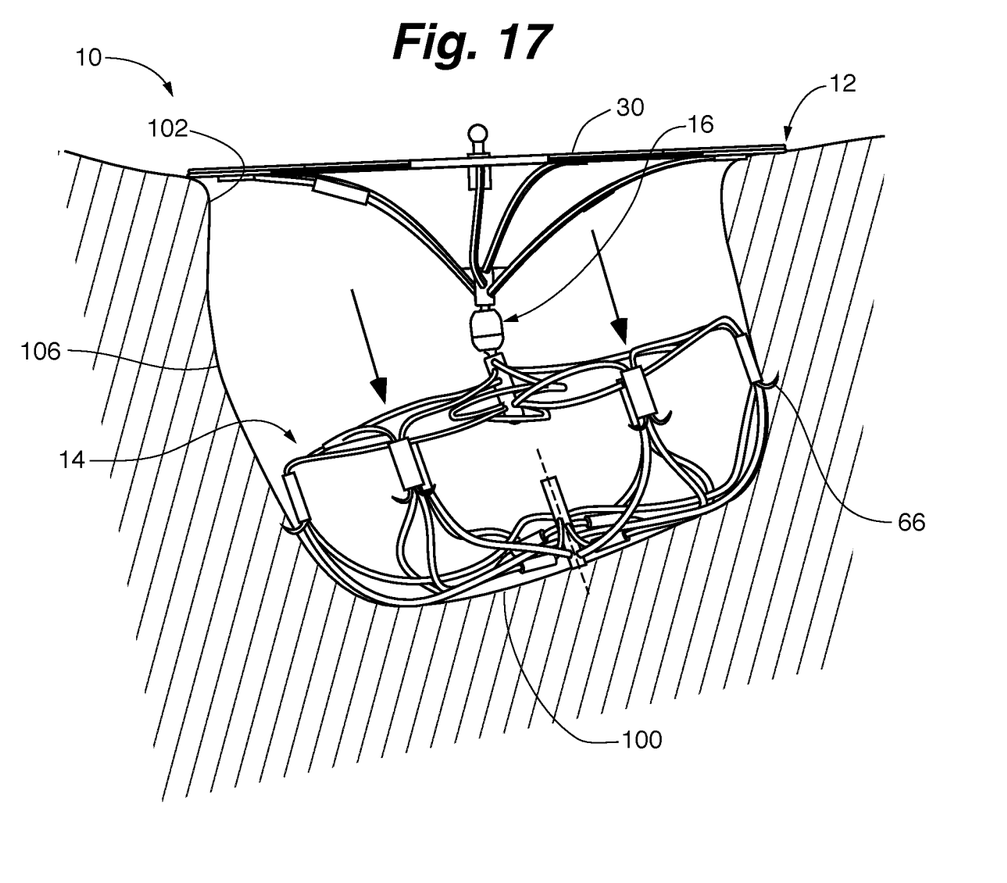
FIG. 17 is a side view of the embodiment shown in FIG. 16, wherein the device is shown deployed with the bulb fully within the LAA and the cap extending fully across the ostium.

To illustrate the flexibility as well as the physiologic aspect of the bulb structure 14 on the shape of the LAA 100, the device 10 is shown in FIG. 17 such that even when allowed to fully deploy within the confines of a tortious ostium 102, the bulb structure 14 minimally strains the surrounding tissue 104.

When properly positioned within the LAA 100, such as in the manner shown in FIG. 17, the bulb structure 14, engages the wall 106 of the LAA 100 but does not exert undue pressure or force sufficient to distend the shape of the LAA 100, but rather conforms to the anatomic tortuosity rather than vice versa. Barbs 66 engage the wall to help retain the bulb within the LAA 100. Cap structure 30, as previously described, includes several features to allow and encourage tissue growth therethrough to ensure eventual and compete occlusion of the LAA in the manner desired.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. A medical device to treat the LAA, the medical device having a deployed state and a confined state, the medical device comprising:

a cap, a bulb and a joint assembly therebetween;

the cap having a plurality of layers, one of the layers defining a base layer, the base layer constructed of at least two sections of mesh material immediately adjacent to one another, a plurality of proximal wire loops extending from the cap to a proximal post of the joint assembly;

the bulb having a plurality of distal wire loops that extend between a terminal post and a distal post of the joint assembly, adjacent distal wire loops being connected one to another by at least one connection collar;

the joint assembly comprising a first ball joint, a second ball joint and a housing, the proximal post extending proximally from the first ball joint, the distal post extending distally from the second ball joint, the housing having a proximal collar and a distal collar, the proximal collar retaining the first ball joint in a first ball and socket relationship, the distal collar retaining the second ball joint in a second ball and socket relationship;

the housing having a housing longitudinal axis extending therethrough, a proximal longitudinal axis extending through the first ball joint and the proximal post, a distal longitudinal axis extending through the second ball joint and the distal post, the first ball and socket relationship allowing the proximal longitudinal axis to form an angle of between about 0 to about 35 degrees with the housing longitudinal axis in any direction, the second ball and socket relationship allowing the distal longitudinal axis to form an angle of between about 0 to about 35 degrees with the housing longitudinal axis in any direction.

2. The medical device of claim 1 wherein in the confined state the device is folded into the interior of a delivery catheter.

3. The medical device of claim 2 wherein the distal wire loops of the bulb are constructed and arranged to self-expand from the confined state to the deployed state within an LAA, the bulb having a diameter, in the deployed state the diameter of the bulb being greater than the diameter in the confined state.

4. The medical device of claim 3, wherein in the deployed state the bulb does not distort the inherent shape of the LAA.

5. The medical device of claim 3 wherein the distal wire loops are constructed of a plurality of strands of shape memory material.

6. The medical device of claim 5 wherein the shape memory material is nitinol.

7. The medical device of claim 3 wherein at least some of the distal wire loops include barbs, the barbs constructed and arranged to engage tissue of the LAA when the bulb is in the deployed state.

8. The medical device of claim 1 wherein the LAA defines an ostium, in the deployed state the cap extending across and completely covering the ostium.

9. The medical device of claim 1 wherein the plurality of layers further comprise, a petal layer and a securement layer, the securement layer being immediately adjacent to an engagement hub, a portion of the engagement hub extending through an opening defined by each of the layers to secure each of the layers to one another to form the cap.

10. The medical device of claim 9 wherein the petal layer is comprised of a plurality of continuous and overlapping petals of a mesh material, the mesh material of the petal layer being the same or different than the mesh material of the base layer.

* * * * *